(12) United States Patent
Panagiotou

(10) Patent No.: US 11,938,456 B2
(45) Date of Patent: Mar. 26, 2024

(54) LAYERED PARTICLES AND PROCESSES THEREOF

(71) Applicant: Delphi Scientific, LLC, Maynard, MA (US)

(72) Inventor: Thomai Panagiotou, Winchester, MA (US)

(73) Assignee: Delphi Scientific, LLC, Maynard, MA (US)

( * ) Notice: Subject to any disclaimer, the term of this patent is extended or adjusted under 35 U.S.C. 154(b) by 1261 days.

(21) Appl. No.: 16/470,136

(22) PCT Filed: Dec. 18, 2017

(86) PCT No.: PCT/US2017/066985
§ 371 (c)(1),
(2) Date: Jun. 14, 2019

(87) PCT Pub. No.: WO2018/112456
PCT Pub. Date: Jun. 21, 2018

(65) Prior Publication Data
US 2020/0016562 A1    Jan. 16, 2020

Related U.S. Application Data

(60) Provisional application No. 62/435,514, filed on Dec. 16, 2016.

(51) Int. Cl.
*A61K 9/50* (2006.01)
*B01F 23/41* (2022.01)
*B01F 23/45* (2022.01)
*B01F 23/80* (2022.01)
*B01J 2/00* (2006.01)
*B01J 13/04* (2006.01)
*B01F 29/00* (2022.01)

(52) U.S. Cl.
CPC ............... *B01J 13/04* (2013.01); *A61K 9/501* (2013.01); *A61K 9/5036* (2013.01); *A61K 9/5073* (2013.01); *B01F 23/41* (2022.01); *B01F 23/45* (2022.01); *B01F 23/808* (2022.01); *B01J 2/006* (2013.01); *B01F 23/413* (2022.01); *B01F 23/4146* (2022.01); *B01F 29/00* (2022.01)

(58) Field of Classification Search
None
See application file for complete search history.

(56) References Cited

U.S. PATENT DOCUMENTS

| | | |
|---|---|---|
| 5,187,554 A | 2/1993 | Miwa |
| 5,269,980 A | 12/1993 | Levendis et al. |
| 5,593,875 A | 1/1997 | Wurn et al. |
| 8,187,554 B2 | 5/2012 | Panagiotou et al. |
| 8,367,004 B2 | 2/2013 | Panagiotou et al. |
| 8,431,221 B2 | 4/2013 | Bell et al. |
| 9,050,249 B2 | 6/2015 | Yoshida et al. |
| 2005/0016851 A1 | 1/2005 | Jensen et al. |
| 2005/0129580 A1 | 6/2005 | Swinehart et al. |
| 2008/0171090 A1 | 7/2008 | Yagi et al. |
| 2008/0226704 A1 | 9/2008 | Kigoshi et al. |
| 2009/0035381 A1 | 2/2009 | Stankus et al. |
| 2015/0335753 A1 | 11/2015 | Desai et al. |

FOREIGN PATENT DOCUMENTS

| | | |
|---|---|---|
| EP | 3554478 A1 | 10/2019 |
| WO | 2005089926 A1 | 8/2007 |
| WO | 2011140627 A1 | 11/2011 |
| WO | 2015057998 A1 | 4/2015 |
| WO | 2016010840 A1 | 1/2016 |
| WO | 2016138175 A1 | 9/2016 |

OTHER PUBLICATIONS

International Preliminary Report on Patentability; The International Bureau of WIPO; International Application No. PCT/US2017/066985; dated Jun. 18, 2019; 14 pages.
Mauro Ferrari; Cancer Nanotechnology: Opportunities and Challenges; Nature Reviews; Mar. 2005; 11 pages; vol. 5.
Andrew Fire et al; Potent and Specific Genetic Interference by Double-Stranded RNA in Caenorhabditis Elegans; Nature; Feb. 19, 1998; 8 pages; vol. 391.
Elisabeth V. Giger; Stabilization of Calcium Phosphate Nanoparticles for Transfection with Nucleic Acid Drugs; DISS. ETH No. 20625; 2012; 180 pages; Zurich, Switzerland.
Yang Yang et al; Systemic Delivery of siRNA via LCP Nanoparticle Efficiently Inhibits Lung Metastasis; Molecular Therapy; Mar. 2012; 7 pages; vol. 20 No. 3.
Microfluidics International; www.microfluidicscorp.com; 3 pages.
Thomai Panagiotou et al; Production of Norfloxacin Nanosuspensions Using Microfluidics Reaction Technology through Solvent/Antisolvent Crystallization; Ind. Eng. Chem. Res.; 2009; 12 pages; vol. 48.
T. Panagiotou et al; Microfluidics Reaction Technology (MRT) for Continuous Production for Nano-Formulations of Drug Entities and Advanced Materials; NanoFormulation; 2012; 15 pages.
Thomai Panagiotou et al; Bottom up Nano-Particle Formation via Controlled Crystallization and Chemical Reactions; MRS Proceedings; 2011; 12 pages.
T. Panagiotou et al; Production of Polymer Nanosuspensions Using Microfluidizer Processor Based Technologies; NSTI-Nanotech; 2008; 4 pages.
S. Saha et al; Recent Developments in Multilayered Polymeric Particles—From Fabrication Techniques to Therapeutic Formulations; Journal of Materials Chemistry B; 2013; 14 pages.
Agnes Miseur et al; Rotavirus Double and Triple Layered Viral Particles: Correlative Characterization Using Electron Microscopy, Disc Centrifuge and Capillary Electrophoresis; 2 pages; DOI: 10.1002/9783527808465.EMC2016.6086.

(Continued)

*Primary Examiner* — H. Sarah Park
(74) *Attorney, Agent, or Firm* — Taft Stettinius & Hollister LLP

(57) ABSTRACT

Process for the preparation of layered particles are provided. Layered particles prepared by such processes are also provided.

19 Claims, 8 Drawing Sheets

(56) References Cited

OTHER PUBLICATIONS

M. Badila et al; Design of Colored Multilayered Electrophoretic Particles for Electronic Inks; Applied Materials & Interfaces; 2011; 9 pages; vol. 3.
Sampa Saha et al; Application-Drive Multi-Layered Particles—The Role of Polymers in the Architectural Design of Particles; Elsevier; Polymer; 2015; 11 pages; vol. 71.
chemeurope.com; Technique Mass-Produces Uniform, Multilayered Particles; 3 pages; www.chemeurope.com.
T. Panagiotou et al; Production of Stable Drug Nanospensions Using Microfluidics Reaction Technology; NSTI—Nanotech 2007; www.nsti.org; ISBN 1420063766; vol. 4; pp. 246-249; 2007.
B. Guiffard et al; Low temperature synthesis of stoichiometric and homogeneous lead zirconate titanate powder by oxalate and hydroxide coprecipitation; Materials Research Bulletin; vol. 33; Issue 12; Dec. 1998; pp. 1759-1768.
Kolmogorov; The Local Structure of Turbulence in Incompressible Viscous Fluid for Very Large Reynolds Numbers; Proc. USSR Acad. Sci. 1941; 30; 299-303.
Kirkland; Porous Thin-Layer Modified Glass Bead Supports for Gas Liquid Chromatography; Analytical Chemistry; 1965; 37; 1458; doi:10.1021/ac60231a004.
Iler; Multilayers of colloidal particles; Journal of Colloid and Interface Science; 21; 569; doi: 10.1016/0095-8522(66)90018-3.
International Search Report and Written Opinion, International Patent Application No. PCT/US2017/066985, dated Feb. 15, 2018, 15 pages.
Office Action; Israel Patent Office; Israel Application No. 267102; dated Feb. 1, 2022; 3 pages.
Office Action; Japanese Patent Office; Japanese Application No. 2019-532921; dated Sep. 29, 2021; 6 pages.
Extended European Search Report; European Patent Office; European Patent Application No. 17882186.4; dated Jul. 28, 2020; 8 pages.
Communication Pursuant to Rules 70(2) and 70a(2) EPC; European Patent Office; European Patent Application No. 17882186.4; dated Aug. 14, 2020; 1 page.

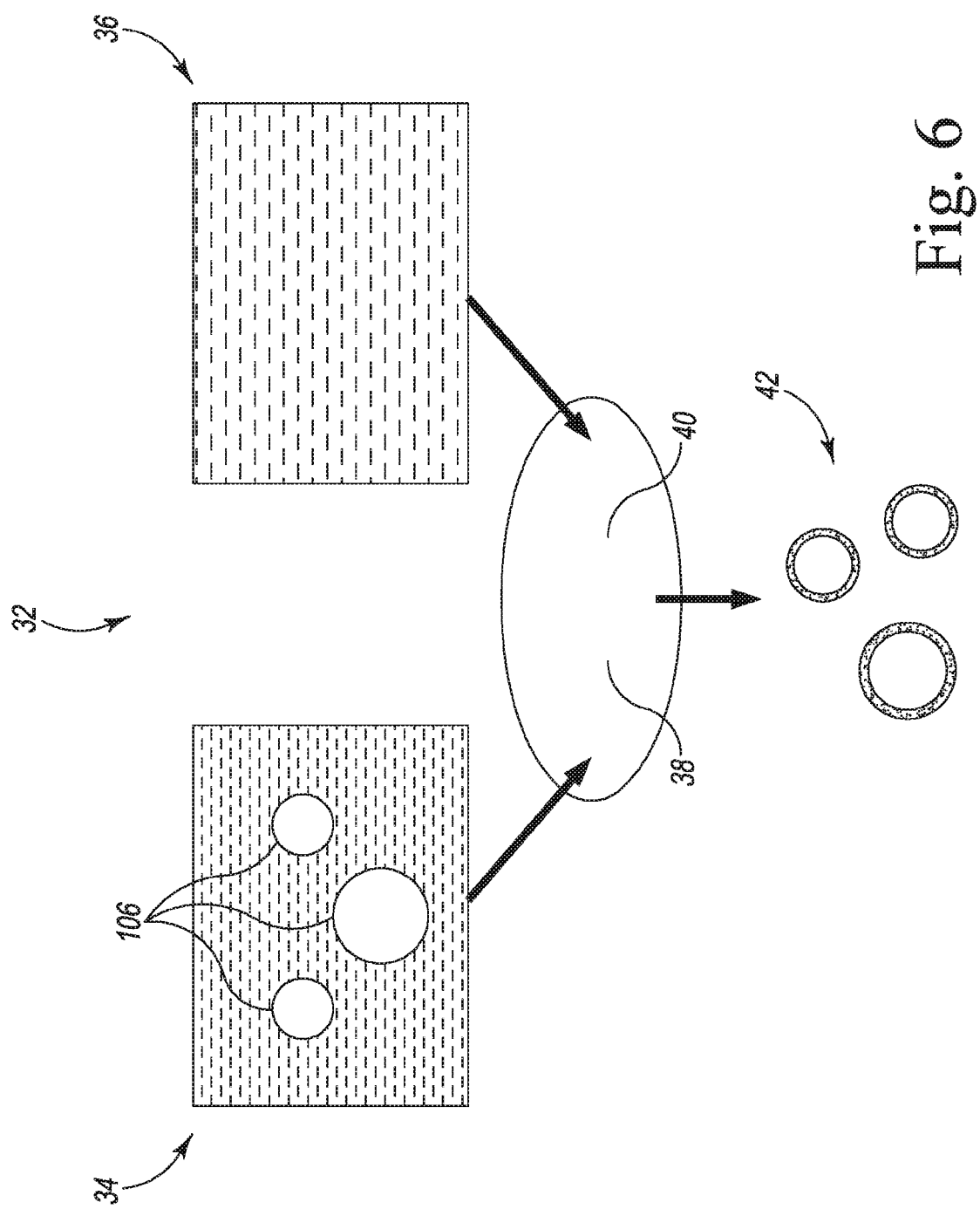

LAYERED PARTICLES AND PROCESSES THEREOF

CROSS-REFERENCE TO RELATED APPLICATIONS

This application is a U.S. National Phase of International PCT Application No. PCT/US2017/066985 filed Dec. 18, 2017, which claims the benefit of U.S. Patent Application Ser. No. 62/435,514 filed Dec. 16, 2016, the contents of each application are incorporated herein by reference in their entirety.

FIELD

The present disclosure provides layered small particles that may have complex functionalities, along with processes for manufacturing such particles.

BACKGROUND

Small particles have applications in many different industries, including without limitation the pharmaceutical, food, energy, and fine chemical industries. Because of their size, such particles are capable of reducing diffusion limitations, and therefore may allow the particles (bound to molecules of interest) to move more easily across different boundaries. For example, in the pharmaceutical industry, small particles are often used for enhancing the delivery rates of biologically active ingredients that would otherwise be difficult to deliver, including without limitation hydrophobic drugs that tend to have poor solubility in water.

Additionally, in some cases, biologically active ingredients benefit from being encapsulated within small particles to protect them until they are in close proximity to their intended biological or molecular target. In those cases, the circumstances and timing of the release of the active ingredient need to be precisely controlled. Unfortunately, using conventional encapsulation technology, the active ingredient may prematurely separate from the particles and migrate to the surface before the biological target is reached. Because of this tendency, there is a need to prevent the active ingredient from early release from small particle carriers in order to retain their desired biological activity.

Delivery of certain types of biologically active ingredients pose significant challenges, including without limitation DNA, RNA, and RNA interference (RNAi) agents, (such as small interfering RNA (siRNA) or micro interfering RNA (miRNA) agents. Recently, there has been great interest in delivering fragments of RNA (including siRNA and miRNA) and DNA for the treatment of various decreases. However, naked RNA and DNA agents can be toxic and are readily attacked by the immune system of the body. As a result, the in vivo efficacy has not lived up to expectations based on in vitro results and serious side effects have also been observed.

In particular, RNA-based therapeutics have garnered significant attention in recent years due to their potential to treat a variety of chronic diseases such as cardiovascular, kidney, oncology, infectious, inflammatory, and metabolic diseases. The promise of RNA therapeutics is linked to their excellent gene silencing potential, high target specificity, and preliminary positive results seen in early stage clinical trials. In addition, the ease of producing such therapeutics with high purity has contributed to their widespread popularity. Industry Analysis and Forecast, 2014-2020, suggests that the RNA based therapeutics market should reach $1.2 billion by 2020, registering a compound annual growth rate of 28.4% during 2014-2020. However, RNA therapeutics will likely never reach their full potential unless improved delivery technology is developed.

RNAi represents an area of RNA therapeutics that would benefit greatly from improved delivery technology. RNAi was first discovered in plants, but it was not widely noted in animals until Andrew Fire and Craig Mello demonstrated that double-stranded RNA can cause greater suppression of gene expression than single-stranded RNA in *Caenorhabditis elegans* [3]. The RNAi approach utilizes short nucleotide sequences (for example, 20-30 nucleotides) that selectively bind to their target messenger RNA in the RNA-induced silencing complex (RISC) to promote their degradation, thereby mitigating the expression of the corresponding gene. Despite the promise of this approach, delivering RNAi agents remains a major barrier to the widespread use of RNAi therapeutics in a clinical setting.

A number of small particle-based formulations have been developed in the past, but they have suffered from various problems and as a result, have not been adopted for widespread use. Often, nano- and micron-size particles in these formulations lacked the complex functionality required to survive inhospitable environments or to perform effectively once they successfully reach their targets. To achieve the required functionality needed for optimal activity, it would be desirable to create layered particles. In theory, a particle having one or more layers could be utilized and each layer could provide the particle with a different functionality designed for a specific purpose. For example, layered particles could provide protection for an active ingredient from oxidation, sequential delivery of multiple active ingredients from a single layered particle, modification of the surface properties of the particles to enhance biocompatibility, or provide stealthiness in a reactive biological environment.

Complex layered particles undoubtedly require more complex manufacturing processes than what is typically used to manufacture simpler particles. For these complex processes to be used on a commercial scale or under the controlled conditions required for pharmaceutical manufacturing, the processes need to be efficient, amenable to scale up, and compliant with current good manufacturing practices (cGMP). One process currently used to produce layered particles to deliver biologically active ingredients (including RNA and DNA) uses calcium phosphate. In theory, calcium phosphate is a desirable starting material for biologically active small particles. Calcium phosphate is benign and already exists in the body. Additionally, calcium phosphate is positively charged, which matches well with the negative charge of the RNA and DNA fragments. However, calcium phosphate particles have significant drawbacks. For example, calcium phosphate particles (1) are notoriously unstable, (2) may not allow for complete encapsulation or full protection of the active agent, and (3) are difficult to manufacture on a large scale or under conditions appropriate for pharmaceutical manufacturing. As a result, there have been no clinical studies using calcium phosphate micro- or nanoparticle formulations to deliver RNA or DNA therapeutics. For the most part, the formulations used by developers of these therapies use lipid particles instead, which have other well-known problems, including toxicity from cationic lipids and liver interactions.

Currently, formulations containing multi-functional particles are primarily based only on surface functionalization, rather than use of multiple layers. For example, Ferrari [1] describes particles containing active ingredients in a polymer matrix. The surface then is functionalized to improve stealthiness and targeting. However, there is only a single vesicle in which the active ingredients reside. Such particles are used by several pharmaceutical companies.

U.S. Pat. No. 5,593,875 [2] describes the formation of calcium phosphate particles for transfection. These particles are formed by simply mixing dilute liquid solutions of the reactants. The particles are allowed to grow passively for a period of time and then the liquid is diluted to stop the particle growth, while simultaneously cells to be transfected are added to the dilute solution. The particles described have several drawbacks: these particles (1) do not have layers, (2) are produced in dilute solutions, (3) have growth that cannot be easily controlled, and (4) must be used simultaneously with final dilution that stops the growth. As a result, this process, in addition to being inefficient, would not be practical for use in a clinical setting.

Elizabeth Verena Giger in reference [4], explores processes for functionalizing the surface of calcium phosphate particles to enhance stability. However, the particles are produced by uncontrolled mixing of very dilute solutions of the reactants.

Yang et al. in reference [5] describes a process to produce calcium phosphate nanoparticles in water-in-oil emulsions inside organic solvents. However, this process requires large volumes of hazardous solvents to be used and is difficult to scale up.

There continues to be a need for new layered particles to deliver active ingredients in a controlled and effective manner. In addition, there is an ongoing need for processes to produce particles that are amendable to scaled up manufacturing and can be used for production of pharmaceuticals and other products that require an efficient, scalable, and well-controlled manufacturing process.

SUMMARY

The present disclosure addresses the problems described above by providing processes for the preparation of layered particles.

Another aspect of the present disclosure provides particles prepared by the processes of the present disclosure. Other embodiments are also disclosed.

The processes of the present disclosure allow for building one or more layers on small particles with precise dimensions. These processes can generate particles having concentrations that are higher than the concentrations using conventional processes, therefore, increasing the efficiency of the manufacturing process. In addition, the processes of the present disclosure avoid the use of organic solvents and can completely encapsulate the active ingredient by creating one or more layers around the particle. Furthermore, the processes of the present disclosure can create one or more layers on the surface of the particles that can modify surface and release properties of the active ingredient(s), as desired. As a result, the layered particles according to the present disclosure are capable of delivering precise amounts of active ingredients in a controlled and effective manner.

BRIEF DESCRIPTION OF DRAWINGS

The above-mentioned aspects of embodiments will become more apparent and will be better understood by reference to the following description of the embodiments taken in conjunction with the accompanying drawings, wherein:

FIG. 6 shows a process of preparing layered particles in accordance with an embodiment.

DESCRIPTION

Figure 1:
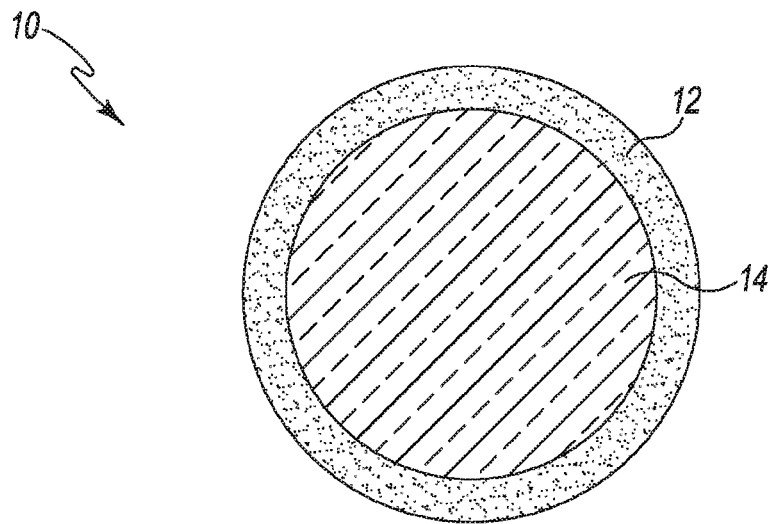
FIG. 1 shows a layered particle in accordance with an embodiment.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

One aspect of the present disclosure provides a process for the preparation of layered particles. In some embodiments, the process comprises:
(a) forming a first liquid stream comprising:
(i) introducing one or more core particles into a first liquid carrier;
(ii) mixing the one or more core particles in the first liquid carrier to form a first mixture;
(iii) optionally, homogenizing the first mixture; and
(iv) introducing one or more reactants into the first mixture;
(b) forming a second liquid stream comprising:
(i) introducing one or more reactants into a second liquid carrier;
(ii) mixing the one or more reactants in the second liquid carrier to form a second mixture; and
(iii) optionally, homogenizing the second mixture;
(c) continuously pumping the first liquid stream into a first port of a multi-port homogenizer, rotor-stator mixer or microreactor, wherein the first liquid stream is pumped into the homogenizer, rotor-stator mixer or microreactor at a fraction of the flow rate of the homogenizer, rotor-stator mixer or microreactor;
(d) continuously pumping the second liquid stream into a second port of the multi-port homogenizer, rotor-stator mixer or microreactor; and
(e) mixing the first liquid stream and the second liquid stream inside the homogenizer, rotor-stator mixer or microreactor for an effective period of time to form a layer on the one or more core particles.

In some embodiments, step (a)(iv) further comprises introducing one or more surfactants into the first mixture. In some embodiments, step (b)(i) further comprises introducing one or more surfactants into the second liquid carrier. In some embodiments, step (a) further comprises washing the one or more core particles. As used herein, the term "layered particles" means core particles having one or more layers.

In some embodiments, step (b) further comprises washing the one or more core particles.

As used herein, the term "effective period of time" is that period of time that sufficiently mixes the first liquid stream and the second liquid stream to form a layer on the one or more core particles. In some embodiments, the effective period of time is from about 1 microsecond to about 1 hour. In other embodiments, the effective period of time is from about 1 microsecond to about 20 seconds. In other embodiments, the effective period of time is from about 1 microsecond to about 1 minute. In other embodiments, the effective period of time is from about 1 microsecond to about 100 microseconds. In some embodiments, the effective period of time is from about 10 microseconds to about 90 microseconds.

In some embodiments, the process of the present disclosure further comprises suspending the one or more core particles in a solution. In some embodiments, the process of the present disclosure further comprises deagglomerating the one or more core particles. In some embodiments, the process further comprises suspending the one or more layered particles in a solution. In some embodiments, the process of the present disclosure further comprises deagglomerating the one or more layered particles.

In some embodiments, step (e) further comprises washing the one or more layered particles. In some embodiments, the process of the present disclosure further comprises repeating steps (a)(iv) and (b)(iii) to step (e) to increase the thickness of the layer. In some embodiments, the process of the present disclosure further comprises repeating steps (a) to (e) to form a second layer.

In some embodiments, the process of the present disclosure further comprises suspending the one or more layered particles in a solution. In some embodiments, the process of the present disclosure further comprises deagglomerating the one or more layered particles. In some embodiments, the process of the present disclosure further comprises filtering the mixture to remove particles having sizes from about 200 nanometers (nm) to about 25 microns.

In some embodiments, the process of the present disclosure further comprises sterilizing the mixture.

In some embodiments, the process of the present disclosure further comprises lyophilizing the one or more layered particles. In some embodiments, the process of the present disclosure further comprises drying the one or more layered particles. In some embodiments, the process of the present disclosure further comprises heat treating the one or more layered particles.

In some embodiments, the one or more reactants in the first liquid stream are acids. In some embodiments, the one or more reactants in the first liquid stream are bases. In some embodiments, the one or more reactants in the second liquid stream are bases. In some embodiments, the one or more reactants in the second liquid stream are acids. In some embodiments, the acids and bases react to form a salt. In some embodiments, the reactants in the first liquid stream and the second liquid stream are salts. In some embodiments, the salts react to form another salt.

In some embodiments, the same liquid is used in the first liquid stream and the second liquid stream. In some embodiments, a different liquid is used in the first liquid stream and the second liquid stream. In some embodiments, the layered particles comprise crystalline solid particles. In some embodiments, the layered particles comprise amorphous solid particles. In some embodiments, the layered particles comprise solid, liquid or semi-solid particles.

In some embodiments, the layered particles are selected from small molecules, nucleic acids, proteins, peptides, and monoclonal antibodies. In some embodiments, one or more active pharmaceutical ingredients are encapsulated in the layered particles. In some embodiments, one or more active pharmaceutical ingredients are embedded in matrices within the layered particles. In some embodiments, the matrices are selected from polymers, metal oxides, organic salts, inorganic salts, lipids, oils, and waxes.

In some embodiments, the one or more core particles or one or more layers include without limitation one or more of the following or the derivatives thereof:
a) Polymers: poly(lactic acid) (PLA), poly(lactide-co-glycolide) (PLGA), poly(epsilon-caprolactone) (PCL), starches, polysaccharides, biocompatible polymers, poly(acrylates), and poly(styrene), crosslinked polymers, alginates, polymers containing PES (pegylated polymers), and derivatives thereof;
b) Lipids: cholesterol, phospholipids, lecithin, soybean lecithin, egg lecithin, cationic lipids, neutral lipids, and sterols, and derivatives thereof. In some embodiments, the one or more liquids are selected from lipids containing poly(ethylene glycol) (pegylated), fluorescent lipids, and crosslinking lipids;
c) Gelatin, sucrose, dextrose, RNA, DNA, species containing nucleic acids, peptides, proteins, monoclonal antibodies, small molecule drugs, curcumin, plant sterols, carotenoids, and vitamin C;
d) Vegetable oil, soybean oil, olive oil, canola oil, corn oil, palm oil, sesame oil, vitamin E, nut oils, fish oil, omega-3 containing oils, monoglycerades, oligoclycerades, polyglycerades, vitamin A, vitamin K, oleic acid, mineral oil, squalene, squalene, essential oils, waxes, perfluorocarbons, perfluodecalene, and FC-43;
e) Sodium chloride, sodium carbonate, sodium phosphate, sodium salts, calcium carbonate, calcium phosphate, calcium salts, magnesium phosphate, aluminosilicates, silica, alumina, zirconia, metal oxides, barium titanite, PZT (Lead Zirconium Titanate), carbon, graphite, glassy carbon, amorphous carbon, gold, silver, platinum, palladium, metal particles, and derivatives thereof;
f) Cancer drugs, antibiotics, anesthetic drugs, anti-inflammatory, ocular drugs, vaccines, adjuvants, and pain medication; and
g) Polysorbates, Tween80, Tween 20, Tween 60, Polyoxyethylene octyl phenyl ether, Triton-X 100, Igepal CA-630, various Kolliphor™ materials, Soluplus®, Collidon®, Span® 85, sorbitan triolate, albumin, whey protein, xanthan gum, and derivatives thereof.

In some embodiments, the first liquid carrier includes without limitation water, buffer solution, ethanol, methanol, acetone, dimethyl sulfoxide (DMSO), N-Methyl-2-pyrrolidone (NMP), tetrahydrofuran, acetonitrile, poly(ethylene glycol), dichloromethane, heptane and other limonene and 2-methyl tetrahydrofuran (2-MeTHF), glycerol, and derivatives and combinations thereof.

In some embodiments, the one or more reactants include without limitation calcium chloride, calcium carbonate, calcium hydroxide, sodium phosphate, sodium carbonate, calcium nitrate, sodium hydroxide, magnesium hydroxide, sodium silicate, aluminum, aluminum sulfate, benzoyl peroxide, ammonia, nitric oxide, stearic acid, hydrochloric acid, sulfuric acid, silica, zinc nitrate, furfuryl alcohol, zinc parathion, and zirconium oxychloride.

In some embodiments, the second liquid carrier includes without limitation water, buffer solution, ethanol, methanol, acetone, dimethyl sulfoxide (DMSO), N-Methyl-2-pyrrolidone (NMP), tetrahydrofuran, acetonitrile, poly(ethylene glycol), dichloromethane, heptane and other limonene and 2-methyl tetrahydrofuran (2-MeTHF), glycerol, and derivatives and combinations thereof.

In some embodiments, the one or more reactants in the first liquid stream react with the one or more reactants in the second liquid stream when the first liquid stream and second liquid stream are mixed in step (e). In some embodiments, the one or more reactants in the first liquid stream and the one or more reactants in the second liquid stream contain dissolved salts that precipitate when the salts in the first liquid stream and the salts in the second liquid stream come into contact during mixing step (e).

In some embodiments, the salts in the first liquid stream comprise calcium chloride or any other calcium salt and the salts in the second liquid stream comprise sodium phosphate or any other phosphate salt. In some embodiments, the salts in the first liquid stream comprise sodium phosphate and the salts in the second liquid stream comprise calcium chloride.

In some embodiments, the first liquid stream, the second liquid stream, or both the first liquid stream and the second liquid stream further comprise nucleic acids.

In some embodiments, the first liquid stream, the second liquid stream, or both the first liquid stream and the second liquid stream further comprise one or more active pharmaceutical ingredients.

In some embodiments, the first liquid carrier and the second liquid carrier are the same.

In some embodiments, the energy rate of the mixing in step (e) is from about 10 to about $10^{10}$ W/kg.

In some embodiments, the first liquid stream and the second liquid stream are miscible. In some embodiments, the first liquid stream and the second liquid stream are immiscible. In some embodiments, the liquid carrier in the first liquid stream is a solvent and the liquid carrier in the second liquid stream is an anti-solvent. In some embodiments, the liquid carrier in the first liquid stream is an anti-solvent and the liquid carrier in the second liquid stream is a solvent.

In some embodiments, the liquid carrier in the first liquid stream is a solvent and the liquid carrier in the second liquid stream is an anti-solvent. In some embodiments, the liquid carrier in the first liquid stream is an anti-solvent and the liquid carrier in the second liquid stream is a solvent. In some embodiments, the liquid carrier in the first liquid stream is aqueous and the liquid carrier in the second liquid stream comprises one or more water miscible organic solvents having one or more polymers or one or more lipids dissolved in the solvents.

In some embodiments, the one or more solvents comprise water miscible alcohols or water miscible ketones. In some embodiments, the one or more solvents are selected from ethanol, methanol, acetone, dimethyl sulfoxide (DMSO), N-Methyl-2-pyrrolidone (NMP), tetrahydrofuran, acetonitrile, and poly(ethylene glycol). In some embodiments, the one or more polymers are selected from poly(lactic acid) (PLA), poly(lactide-co-glycolide) (PLGA), poly(epsilon-caprolactone) (PCL), starches, polysaccharides, biocompatible polymers, poly(acrylates), and poly(styrene), and derivatives thereof.

In some embodiments, the one or more lipids are selected from cholesterol, phospholipids, cationic lipids, neutral lipids, and sterols, and derivatives thereof. In some embodiments, the one or more liquids are selected from lipids containing poly(ethylene glycol) (pegylated), fluorescent lipids, and crosslinking lipids.

In some embodiments, the first liquid stream, the second liquid stream, or both the first liquid stream and the second liquid stream further comprise one or more active pharmaceutical ingredients. In some embodiments, the layer results from one of precipitation, crystallization, polymerization, crosslinking, an acid-base reaction, a substitution reaction, an oxidation reaction, a reduction reaction, adsorption, and chemisorption.

In some embodiments, the first mixture is selected from a suspension, solution, and an emulsion. In some embodiments, the second mixture is selected from a suspension, solution, and an emulsion.

In some embodiments, the fraction of the flow rate of the homogenizer, rotor-stator mixer or microreactor is from about 0.0001 to about 0.9. In some embodiments, the fraction is from about 0.001 to about 0.9.

Another aspect of the present disclosure provides a process for the preparation of layered particles comprising:
(a) mixing a liquid medium comprising core particles and a liquid carrier to create a mixture;
(b) homogenizing the mixture to deagglomerate the core particles;
(c) separating the mixture into a first liquid stream and a second liquid stream;
(d) introducing one or more reactants into the first liquid stream and one or more reactants into the second liquid stream; and
(e) mixing or homogenizing the first liquid stream and the second liquid stream to react to form a layer.

In some embodiments, the liquid medium further comprises a surfactant. In some embodiments, step (e) further comprises washing the layered particles. In some embodiments, the process of the present disclosure further comprises repeating steps (a) to (e) to form a second layer.

In some embodiments, the same core particles, reactants, and liquid carriers are utilized. In some embodiments, different core particles, reactants, and liquid carriers are utilized.

In some embodiments, the process of the present disclosure further comprises suspending the layered particles in a solution. In some embodiments, the process of the present disclosure further comprises filtering the mixture to remove particles having sizes from about 200 nm to about 25 microns. In some embodiments, the process of the present disclosure further comprises sterilizing the mixture.

In some embodiments, the process of the present disclosure further comprises lyophilizing the layered particles. In some embodiments, the process of the present disclosure further comprises drying the layered particles. In some embodiments, the process of the present disclosure further comprises heat treating the layered particles.

Another aspect of the present disclosure provides a process for the preparation of layered particles comprising:
(a) forming a first liquid stream comprising:
  (i) introducing one or more core particles into a first liquid carrier;
  (ii) mixing the one or more core particles in the first liquid carrier to form a first mixture;
  (iii) optionally, homogenizing the first mixture; and
  (iv) introducing one or more reactants into the first mixture;
(b) forming a second liquid stream comprising:
  (i) introducing one or more core particles into a second liquid carrier;
  (ii) mixing the one or more core particles in the second liquid carrier to form a second mixture;
  (iii) optionally, homogenizing the second mixture; and
  (iv) introducing one or more reactants into the second mixture; and (c) mixing the first liquid stream and the second liquid stream to form a layer on the one or more core particles.

In some embodiments, step (a)(iv) further comprises introducing one or more surfactants into the first mixture. In some embodiments, step (b)(iv) further comprises introducing one or more surfactants into the second mixture. In some embodiments, step (c) further comprises washing the one or more core particles. In some embodiments, the process of the present disclosure further comprises repeating steps (a)(iv) and (b)(iv) to step (c) to increase the thickness of the layer. In some embodiments, the process of the present disclosure further comprises repeating steps (a) to (c) to form a second layer.

Another aspect of the present disclosure provides a process for the preparation of core particles comprising:
(a) forming a first liquid stream comprising:
 (i) introducing one or more reactants into a first liquid carrier to form a first liquid stream; and
 (ii) optionally, homogenizing the first liquid stream;
(b) forming a second liquid stream comprising:
 (i) introducing one or more reactants into a second liquid carrier to form a second liquid stream; and
 (ii) optionally, homogenizing the second liquid stream;
(c) pumping the first liquid stream into a first port of a multi-port homogenizer, rotor-stator mixer or microreactor;
(d) pumping the second liquid stream into a second port of the multi-port homogenizer, rotor-stator mixer or microreactor; and
(e) mixing the first liquid stream and the second liquid stream to form one or more core particles.

In some embodiments, the process of the present disclosure utilizes the core particles to prepare layered particles comprising the steps of:
(a) forming a first liquid stream comprising:
 (i) introducing the one or more core particles into a first liquid carrier;
 (ii) mixing the one or more core particles in the first liquid carrier to form a first mixture;
 (iii) optionally, homogenizing the first mixture; and
 (iv) introducing one or more reactants into the first mixture;
(b) forming a second liquid stream comprising:
 (i) introducing one or more reactants into a second liquid carrier;
 (ii) mixing the one or more reactants in the second liquid carrier to form a second mixture; and
 (iii) optionally, homogenizing the second mixture;
(c) continuously pumping the first liquid stream into a first port of a multi-port homogenizer, rotor-stator mixer or microreactor, wherein the first liquid stream is pumped into the homogenizer, rotor-stator mixer or microreactor at a fraction of the flow rate of the homogenizer, rotor-stator mixer or microreactor;
(d) continuously pumping the second liquid stream into a second port of the multi-port homogenizer, rotor-stator mixer or microreactor; and
(e) mixing the first liquid stream and the second liquid stream inside the homogenizer, rotor-stator mixer or microreactor for an effective period of time to form a layer on the one or more core particles.

In some embodiments, the process of the present disclosure further comprises washing the one or more layered particles. In some embodiments, the process of the present disclosure further comprises repeating steps (a) to (e) to form a second layer.

One of ordinary skill in the art understands that the steps in the processes of the present disclosure can be performed in any order. The ordering of steps varies depending on the conditions desired by the skilled artisan.

Another aspect of the present disclosure provides a layered particle prepared by the processes of the present disclosure.

Another aspect of the present disclosure provides a core particle prepared by the processes of the present disclosure.

In another aspect of the present disclosure, the mixing energy is controlled by the pressure of the homogenizer, rotor-stator mixer or microreactor and the type of processing module. For homogenizer, rotor-stator mixer and microreactors, energy levels of about $10^5$ to about $10^{10}$ W/kg are typical. In some embodiments, the energy levels are 10 to about $10^{10}$ W/kg.

In another aspect of the present disclosure, the contact times of the two streams may vary from about 2 to about 100 microseconds to about 0.5 to about 100 seconds. The precise contact time will depend on a variety of factors, such as the type of homogenizer, rotor-stator mixer or microreactor used. U.S. Pat. No. 5,187,554 [10] supports contact times in the range of 0.5 to 20 seconds. Where a high pressure homogenizer is used, the contact times at the high energy zone tend to be similar (e.g., about 2 to about 100 microseconds).

The layered particles that are formed by the processes of the present disclosure have various characteristics. The Figures show for illustrative purposes only particular characteristics of particles made in accordance with different embodiments of the processes of the present disclosure.

FIG. 1 illustrates a layered particle 10 in accordance with an embodiment. Layered particle 10 includes core 14 having a coating layer 12. Layered particle 10 can be solid, liquid or semi-solid.

Figure 2:
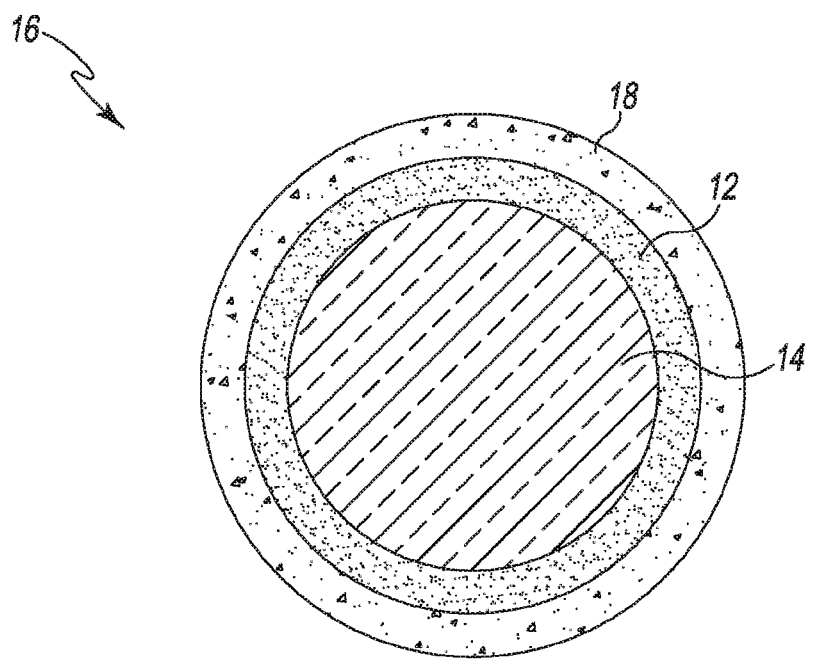
FIG. 2 shows a layered particle in accordance with an embodiment.

FIG. 2 illustrates layered particle 16 in accordance with an embodiment. Layered particle 16 includes core 14 having a coating layer 12 and coating layer 18. Coating layer 12 is surrounding core 14 and coating layer 18 is surrounding coating layer 12. Layered particle 16 can be solid, liquid or semi-solid.

Figure 3:
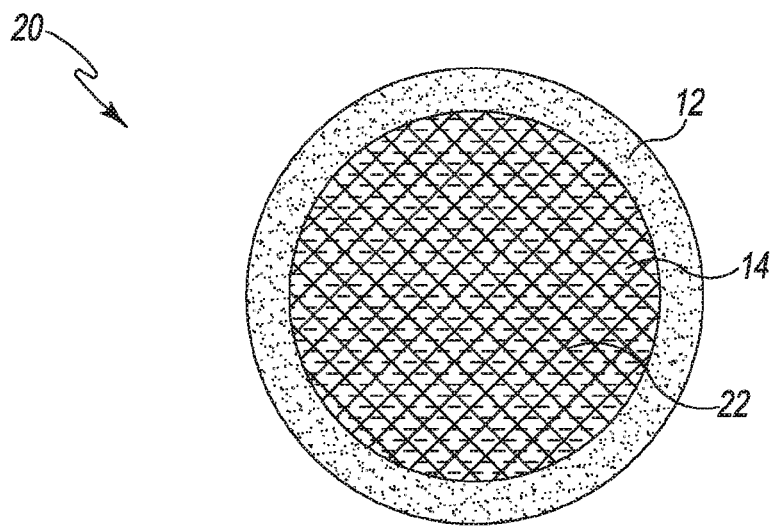
FIG. 3 shows a layered particle in accordance with an embodiment.

FIG. 3 illustrates layered particle 20 in accordance with an embodiment. Layered particle 20 includes core 14, coating layer 12, and matrices containing active ingredient 22 embedded or dissolved within core 14.

Figure 4:
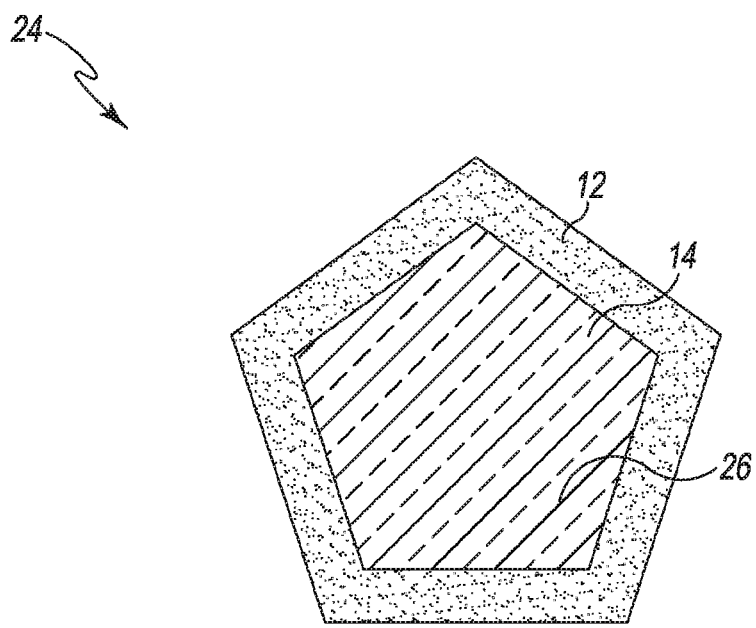
FIG. 4 shows a layered particle in accordance with an embodiment.

FIG. 4 illustrates layered particle 24 in accordance with an embodiment. Layered particle 24 includes core 14, coating layer 12, and crystalline material 26.

Figure 5:
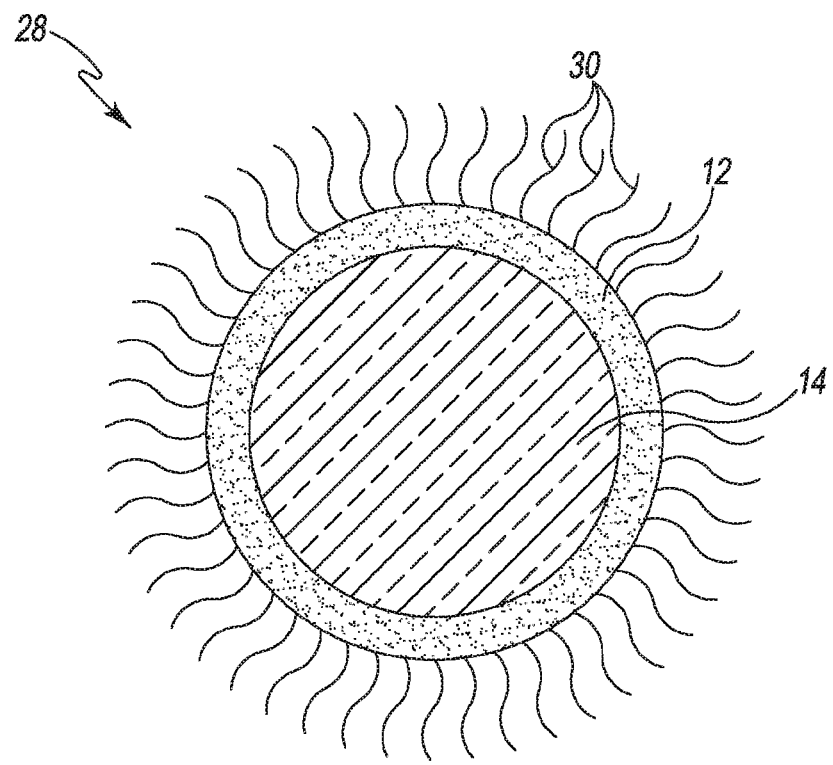
FIG. 5 shows a layered particle in accordance with an embodiment.

FIG. 5 illustrates layered particle 28 in accordance with an embodiment. Layered particle 28 includes core 14, coating layer 12, and polyethylene glycol 30.

FIG. 6 illustrates process 32 of preparing layered particles. In this illustration, liquid stream 34 containing core particles 106 is combined with liquid stream 36 under controlled mixing conditions 38 and controlled time 40 to produce layered particles 42.

Figure 7A:
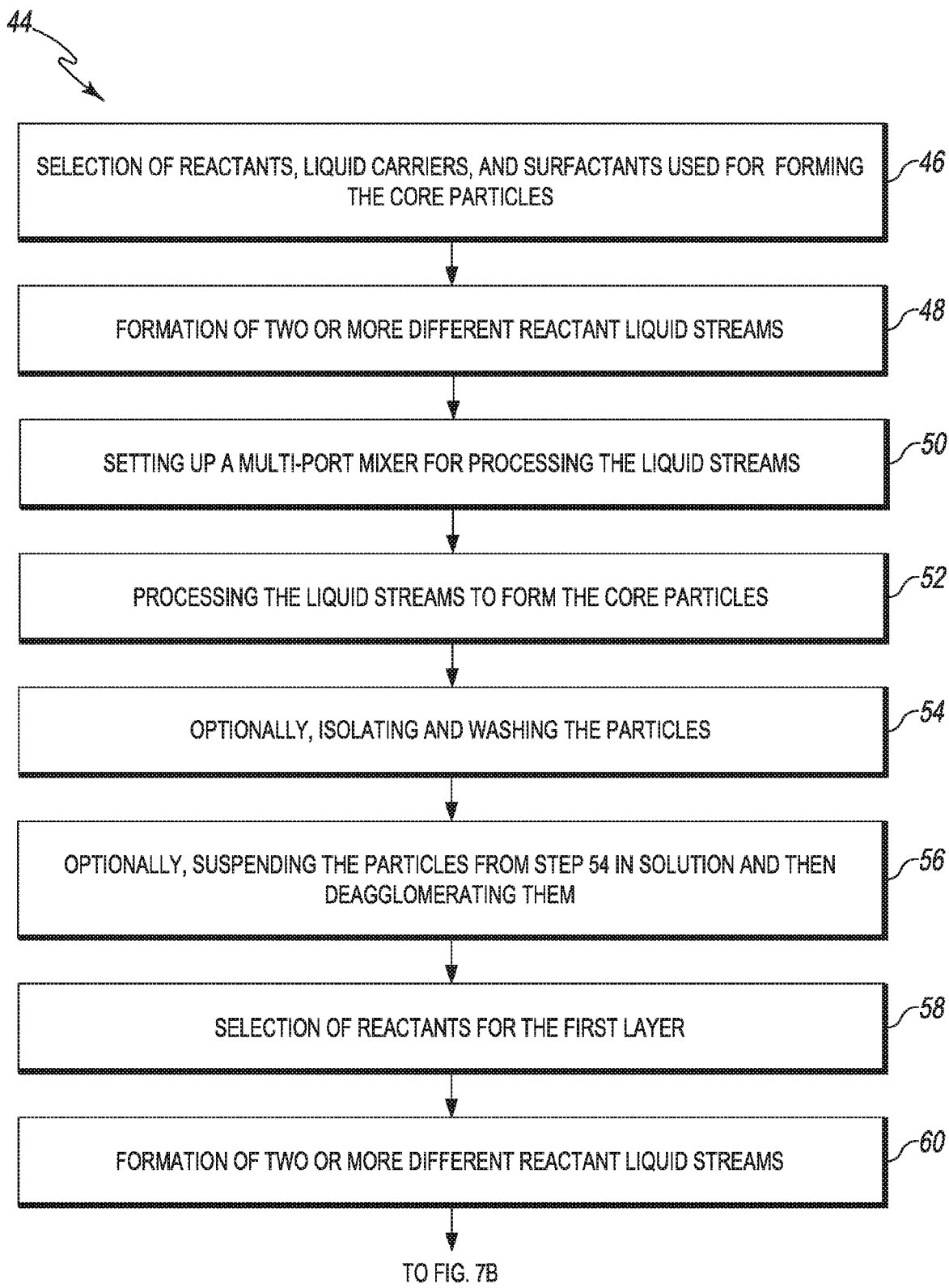
FIG. 7A shows part of a process of preparing layered particles in accordance with an embodiment.

FIG. 7A shows part of a process 44 of preparing layered particles in accordance with an embodiment. Step 46 includes the selection of reactants, liquid carriers and surfactants for forming the core particles. Step 48 involves forming two or more different reactant liquid streams. Step 50 includes setting up the multi-port mixer for processing the liquid streams from Step 48. Step 52 involves processing the liquid streams to form the core particles. Step 54 is an optional step for isolating and washing the core particles. Step 56 is an optional step for suspending and deagglomerating the core particles from Step 54. Step 58 involves selecting the reactants for the first layer. Step 60 involves forming two or more different reactant liquid streams.

Figure 7B:
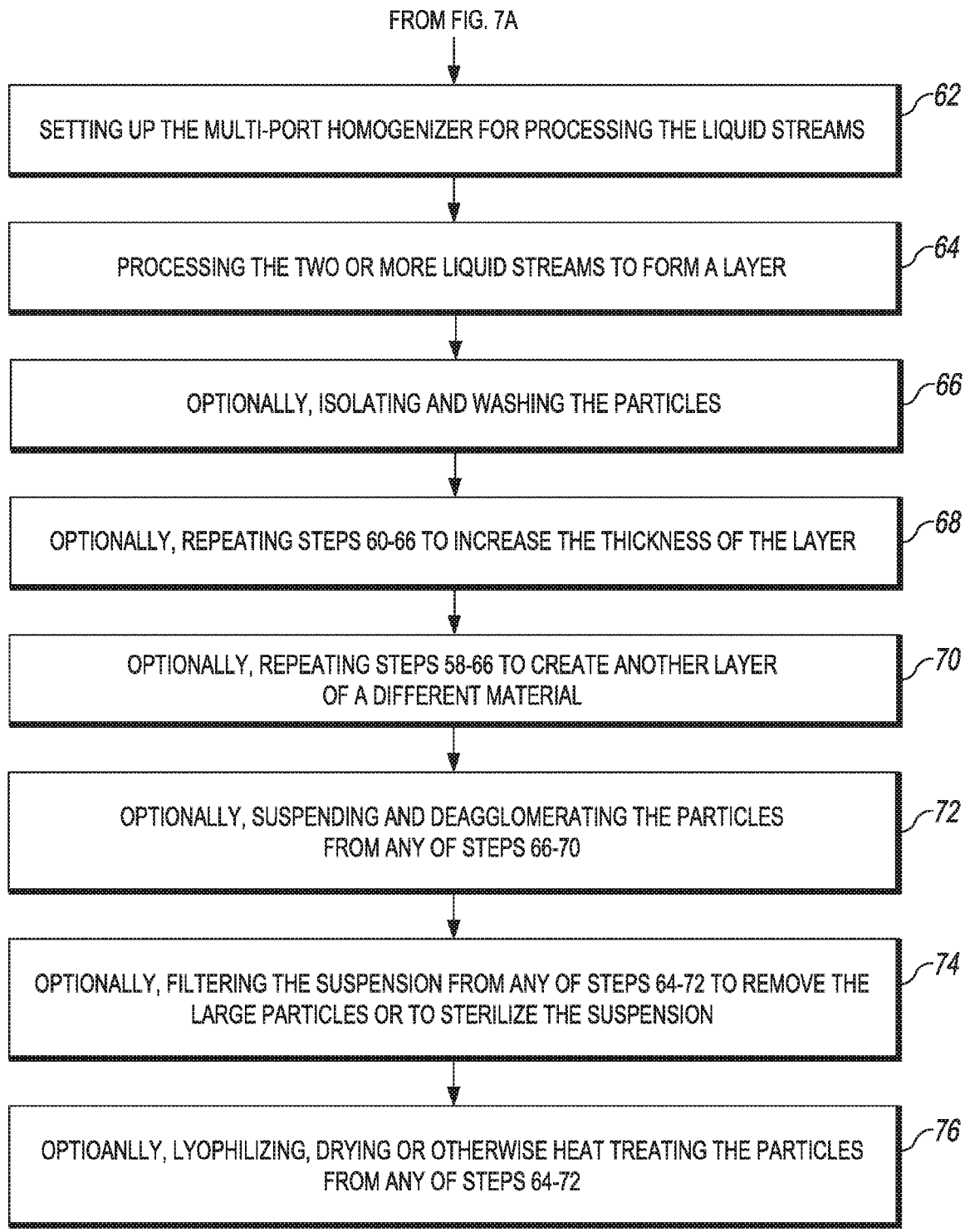
FIG. 7B shows part of a process of preparing layered particles in accordance with an embodiment.

FIG. 7B shows part of a process 44 of preparing layered particles in accordance with an embodiment. Starting after Step 60 shown in FIG. 7A, Step 62 involves setting up the multi-port homogenizer for processing the liquid streams. Step 64 involves processing the liquid streams from Step 60 to form a layer on the particles. Step 66 is an optional step of isolating and washing the particles. Step 68 is an optional step of repeating steps 60-66 to increase the thickness of the layer. Step 70 optionally repeats steps 58-66 to create another layer of a different material. Step 72 is an optional step of suspending and deagglomerating the particles from any one of Steps 66-70. Step 74 is an optional step of filtering the suspension from any of Steps 64-72 to remove large particles or to sterilize the suspension. Step 76 is an optional step of lyophilizing, drying or otherwise heat treating the particles from any one of Steps 64-72.

Figure 8A:
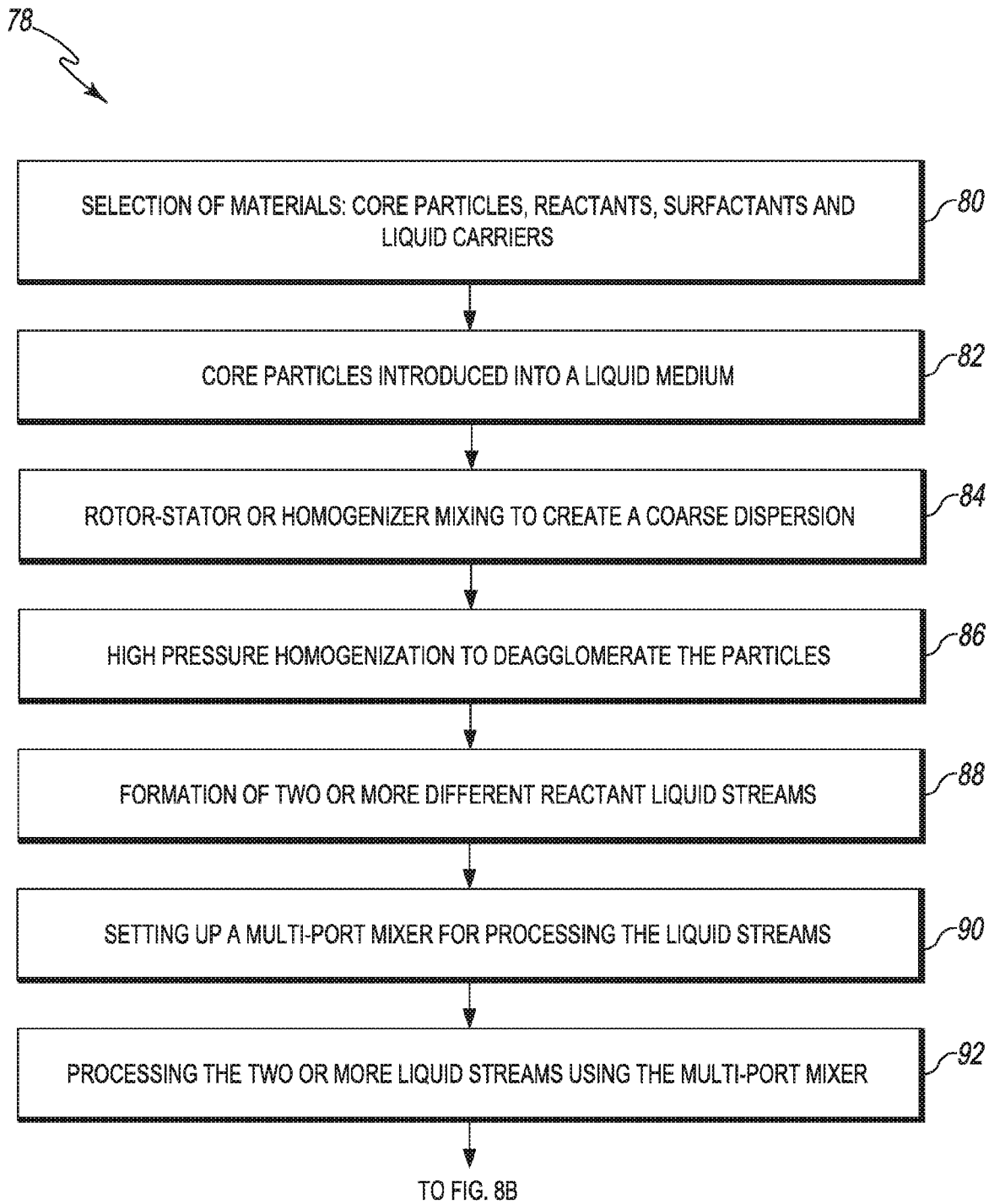
FIG. 8A shows part of a process of preparing layered particles in accordance with an embodiment.

FIG. 8A shows part of a process 78 of preparing layered particles in accordance with an embodiment. Step 80 involves selection of materials such as the core particles, reactants, surfactants and liquid carriers, as further described in this disclosure. Step 82 involves introducing the core particles into a liquid stream. Step 84 involves rotor-stator or homogenizer mixing to create a coarse dispersion. Step 86 involves high pressure homogenization to deagglomerate the particles. Step 88 involves formation of two or more different reactant liquid streams. Step 90 involves setting up a multi-port mixer for processing the liquid streams. Step 92 involves processing the two or more liquid streams from Step 90 using the multi-port mixer.

Figure 8B:
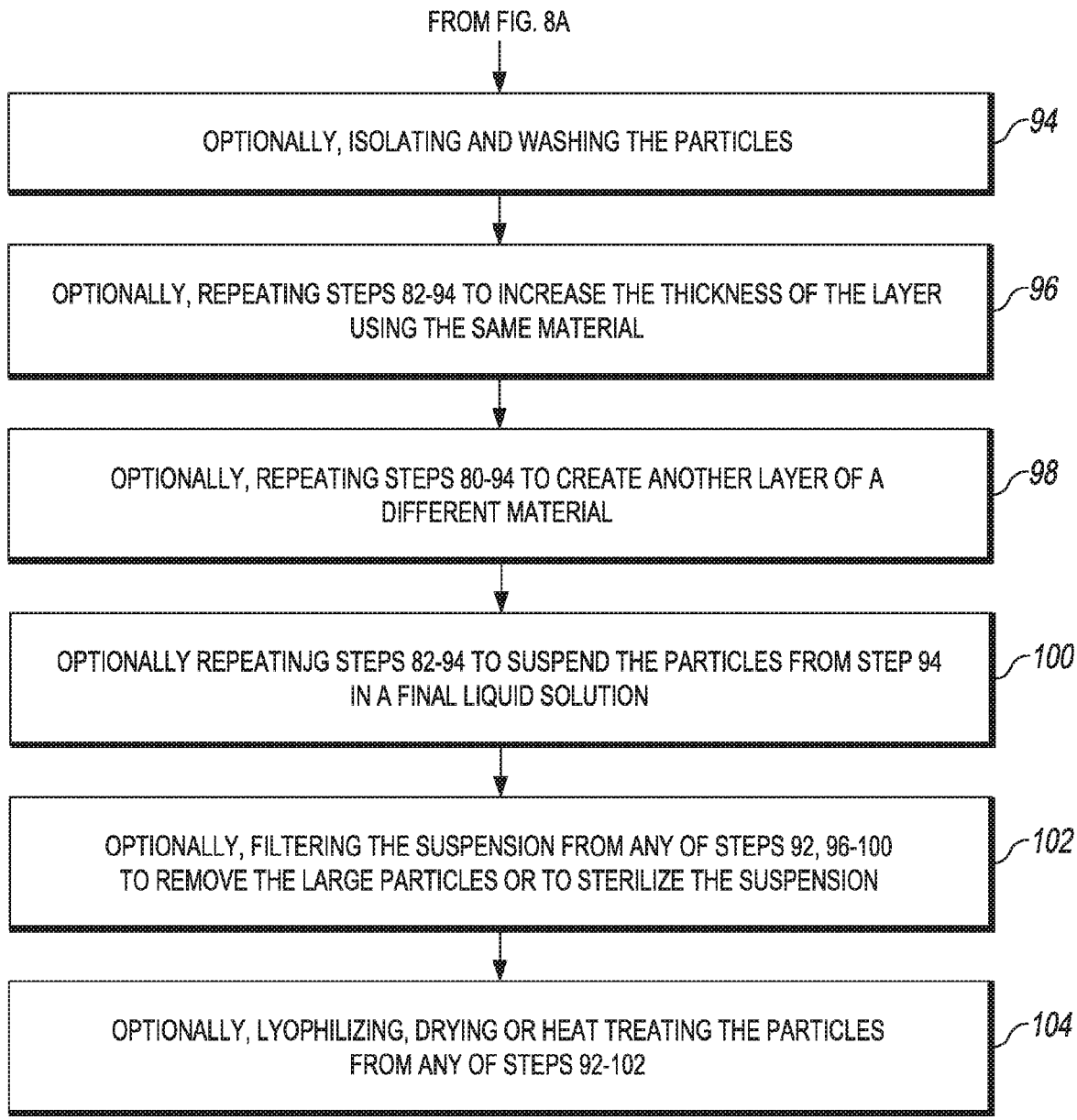
FIG. 8B shows part of a process of preparing layered particles in accordance with an embodiment.

FIG. 8B shows part of a process 78 of preparing layered particles in accordance with an embodiment. Starting with the particles produced in FIG. 8A, Step 94 is the optional step of isolating and washing the particles. Step 96 is the optional step of repeating Steps 82-94 to increase the thickness of the layer using the same material. Step 98 is the optional step of repeating Steps 80-94 to create another layer of a different material. Step 100 is an optional step of repeating Steps 82-94 to suspend the particles from Step 94 in a final liquid solution. Step 102 is an optional step of filtering the suspension from any of Steps 92 or 96-100 to remove the large particles or to sterilize the suspension. Step 104 is an optional step of lyophilizing, drying or otherwise heat treating the particles from any one of Steps 92-100.

The present disclosure also provides various processes for the manufacture of layered particles. The processes of the present disclosure affect key parameters and sub-processes that control the formation of layered particles, including: (a) de-agglomeration of the core particles to expose the surface of the core particles, and (b) forcing the process that leads to layer formation (such as chemical reaction or precipitation) to occur on the particle surface, rather than occurring independent of the particles. The following illustrative steps are typical for the processes of the present disclosure but are not meant to be limiting in any way:

1. Suitable materials are selected: the core particles, the reactants that will be used to form the next particle layer and the carrier liquids in each stream. The core particles may be commercially available or previously made. With respect to reactants, for example, one may be an acid and another is a base and upon reaction they form a salt. The reactants may also be two salts that react via substitution reactions and result in a third salt. There are other options that do not involve chemical reactions, but physical processes, such as precipitation or crystallization. For example, one stream may contain a polymer dissolved in a solvent. The other stream may contain a liquid that is miscible with the solvent, but it does not dissolve the polymer. When these streams combine, the solubility of the polymer is reduced. This may force the polymer to precipitate. Similar to precipitation as described above, is the crystallization process when the dissolved material crystallizes. There may be more than one reactant per stream. The carrier liquids are selected so they are compatible and typically (but not always) miscible. These carrier liquids can be aqueous solutions with various pH, organic solvents, or a combination thereof. They optionally may contain surfactants.

2. Core particles are mixed in a liquid medium. Typical concentrations of the particles in the liquid range from about 0.01 to about 10 wt %, but the particle concentrations may approach about 50%, depending on the materials involved. Optionally, one or more surfactants are mixed in the solution.

3. A rotor stator mixer is used to create a coarse dispersion. For example, an IKA mixer (IKA Works, Inc., 2635 Northchase Parkway SE, Wilmington, NC 28405, USA) may be used, or alternatively a simple rotating propeller that is immersed in the suspension can be used. This step may not completely de-agglomerate the liquid, but creates a suspension that can be further processed. For the rotor-stator mixer the key processing parameters are the rotational speeds and the type of the processing module. Speeds in the range of 500-18,000 rpm are typical, while the processing modules are selected so they are appropriate for the processing dispersions, based on the manufacturer's suggestions.

4. The coarse suspension undergoes high pressure homogenization. The coarse suspension is first poured into the inlet reservoir of a High Pressure Homogenizer (HPH). A pressure is selected to be typically in the range of about 3000 to about 30,000 psi, but it can extend from about 500 psi to about 45,000 psi or more. The type of the processing module of the homogenizer is selected to be suitable for processing dispersions. The processing module, based on the type of the HPH may be, for example, homogenizing valves (APV, Niro Soavi, etc.), reaction chambers (DyHydromatics) or interaction chambers (Microfluidics). The outlet temperature of the processed material is controlled by the heat exchanger that is typically positioned after the processing module. The material may be recirculated several times until deagglomeration is complete, which can be verified using particle size analyzers, optical microscopes, or other means known to those of ordinary skill in the art.

5. Two different liquid streams are formed. The first steam is the suspension, in which one or more of the reactants are dissolved. The other steam contains the other reactant or multiple reactants dissolved in a liquid miscible to the liquid of the first stream. The concentrations of the reactants may be pre-determined based on the reaction type, kinetics and desired thickness of the layer. Each liquid stream is directed in a port of a two-port mixer and is fed at a predetermined rate. There are various mixers that may be used, depending on the application. One is described, for example, in T. Panagiotou, S. Mesite, R. Fisher and I. Gruverman, "Production of Stable Drug Nanospensions Using Microfluidics Reaction Technology". NSTI-Nanotech 2007, www.nsti.org, ISBN 1420063766, Vol. 4, pp. 246-249, 2007, which is incorporated herein by reference in its entirety. This piece of equipment is in effect a dual port homogenizer and is commercially available (model CR5 by Microfluidics, Westwood, MA). There are also dual feed rotor stator mixers, for example, from Quadro Engineering, Ontario, Canada. Additionally, a non-commercially available technology from Microfluidics (MMR) may also be used. Low energy microfluidics reactors such as those from Precision Nanosystems (Vancouver, BC, Canada) may also be used in some situations.

6. The machine is set up. Assuming that a dual port homogenizer is used, like in step 3, the pressure, processing module and temperature are selected. Additionally, the flowrate of one of the streams is controlled using a pump. Since the total flowrate of the machine is controlled by the pressure and the processing module, the flowrate of the second stream adjusts itself, so the sum of the flowrates of the two streams is equal to the total flowrate of the machine. The ratio of the flow rates of the two streams controls the stoichiometry of the chemical reaction of physical process, and therefore control the reaction rates.

7. The layers are created. The HPH machine is turned on and the streams are mixed and react for a predetermined period, typically around 1 second total as they pass through the processing module. The residence time in the high energy zone of the processing module is calculated to be around 10-25 microseconds. Because the chemical reactions/physical processes are completed within these times scales and within the microliter volume of the processing module, the particles get in close proximity with the reactants and subsequently the products of the reaction. Additionally, the processes are expedited because of their small scale (as demonstrated in previous work, see references [7]-[9], for example). The concentrations of the reactants, the pressure, the residence times, the number of passes through the machine and the initial particle size determine the thickness of each layer. Typical thicknesses are about 1-10 nm for particles with initial size below 500 nm.

9. Optionally, the particles are isolated and washed. It may be necessary that the particles are washed in between creating layers, so the reactants and impurities of the previous process are removed. One way to wash those would be to filter the particles and then wash the particles trapped on the filter with a clean liquid solution. Another way would be to separate the particles using a centrifuge and then wash those with a clean solution. Yet another way would be to separate the impurities using hollow fiber tangential filtration. This works best for relatively high MW materials including proteins, RNA, DNA, peptides, etc. Optionally, the thickness of the layer can be increased by repeating steps 5-8.

10. Optionally steps 4-8 or 9 are repeated to create another layer of the same or different material.

11. Optionally Steps 1-3 are repeated to suspend the particles from Step 8 or 9 in a final liquid solution.

12. Optionally the suspension is filtered to remove large particles or to filter sterilize the suspension using known filtering methods.

13. Optionally the particles are lyophilized using methods known to those of ordinary skill in the art.

In addition to the general process steps outlined above, the present disclosure includes process variations that would be well known by those of ordinary skill in the art. Such variations include, without limitation:

(a) The core particles are formed using the dual feed equipment described in step 5, and also publications [6]-[9] and the previous Microfluidics U.S. Pat. No. 8,187,554. These core particles may consist of solid, liquid or semi-solid materials. The following is an example: Solid polymer particles optionally containing an active ingredient are formed via solvent-antisolvent precipitation, as described in Ref. [11]. These form the core particles, while layers are formed at a later stage. It may be possible that the function of the layers is to prevent the active ingredient from leaching out of the particle prematurely.

(b) The core particles are formed simultaneously with at least one of the layer(s). For example, starting on step 4, reactants are selected using both for the core particles and the first layer. If the core particles form via processes that are faster than the processes required for the first layer, then the core particles will form first and the layer material will coat the particles. The following is an example: Liquid particles (droplets) in a liquid medium forming an emulsion, are produced by injecting separately two liquid and immiscible streams, one that forms the discrete phase and the other the continuous phase of the emulsion, as described in reference [8]. One of the liquid streams may contain a polymer, which upon precipitation creates a coating around the droplets, forming nanocapsules.

(c) More than two liquid reactant streams are used in Step 4 to create the coating around the particles. This is useful when multiple processes are taking place and there is a need to keep the reactants separate.

The particles resulting from the process variations above may have different forms. Some of these forms are shown by way of illustration only in the accompanying Figures. For example, FIG. 1 shows a core spherical particle surrounded by a single layer. The core particle may be solid, liquid or semi-liquid. Solid spherical core particles, made out of polymer, may be produced via micro- or nano-precipitation of the polymer in liquid, see reference [11]. They may also be produced as a result of emulsion polymerization or spray drying, see for example U.S. Pat. No. 5,269,980.

The layers may function as a barrier to prevent certain components of the particle from releasing from the particles, or slowing their release rate. For certain applications, there may be a need to coat particles with a layer with specific electrical or electronic properties. As an example, PZT (Lead Zirconium Titanate) is a piezoelectric material that is used in ultrasonic transducers and piezoelectric resonators. For such applications, it may be desirable to utilize particles coated with a PZT layer. The following reference describes the wet chemistry and steps to manufacture PZT. "Low temperature synthesis of stoichiometric and homogeneous lead zirconate titanate powder by oxalate and hydroxide coprecipitation", B. Guiffard and M. Troccaz Materials Research Bulletin Volume 33, Issue 12, December 1998, Pages 1759-1768. In this case, after the co-precipitation there is a heat treatment step.

Liquid particles may form during emulsification. Solid layers around these particles may protect the components of the liquid particle from oxidation, reduce odor, or prevent components from leaching out. Similarly, layers around semi-liquid particles which often include lipids may protect compounds inside the particles.

FIG. 2 shows a particle with multiple layers. It is possible that each layer has a different function. For example, for pharmaceutical applications, the first layer may be used to protect certain compounds inside the core particle. The second layer may be used to create a surface with high biocompatibility, so the particle is accepted and not attached by the immune system.

The core particle of FIG. 3 consists of a matrix with one or more materials embedded or dissolved in. Example would be polymer particles with active ingredients dissolved or embedded in, as mentioned in previous paragraphs. Another example would be a salt, such as calcium phosphate containing RNA, DNA or peptide, molecules. Other examples may include sodium carbonate particles containing protein molecules.

FIG. 4 shows a core particle that is made of a crystalline material and is typically not round in shape. Examples of such materials include solid, small molecule drugs, such as paclitaxel used for treating cancer.

FIG. 5 shows a layered particle with PEGylated species surrounding the particle. Such species are used to stabilize the particles and form a stealthy surface, so the particles for pharmaceutical applications are not detected by the immune system of the body.

A common way to de-agglomerate particles is to suspend them in various liquids, optionally add surfactants, and then use high energy equipment to apply shear forces on the particles. The shear forces help separate the particles from each other, while the presence of surfactants helps keep the particles apart for a long time. The smaller the particles, the higher the required shear forces, as shown later in this section. There are commonly used technologies that deagglomerate the particles, including High Pressure Homogenizers (HPH) and sonicators. Once the particles are deagglomerated, they are ready to get coated. One or more of the reactants that form the coating is mixed in with the particle suspension. This forms the first liquid stream. Another liquid stream is then formed. The second liquid stream contains reactant(s) that react with the reactant(s) in the first liquid stream. The reactants may undergo a chemical reaction and form another species. For example, one may be an acid and another a base and upon reaction they may form a salt. The reactants may also be two salts that react via substitution reactions and result in a third salt. There are other options that do not involve chemical reactions, but physical processes, such as precipitation or crystallization. For example, one stream may contain a polymer dissolved in a solvent. The other stream may contain a liquid that is miscible with the solvent, but it does not dissolve the polymer. When these streams get together, the solubility of the polymer is reduced. This may force the polymer to precipitate. However, the polymer may not precipitate on the particles or coat each particle with a thin layer, unless the chemical reaction or the physical process take place under controlled conditions and precise timing. This may be achieved by using the appropriate equipment that allows for the two streams to mix at the high energy, which is required for forming thin layers around the particles. Additionally, the mixing time will have to match time scale of the chemical reaction or physical process.

Core particles, which serve as a base for the multi-layered particles, can be separated from each other to expose the surface area to be coated. Nano- and micron-size particles have high surface energies and tend to agglomerate or aggregate, which is generally accomplished by utilizing surfactants and dispersing the core particles in liquid applying shear. The level of shear (energy) required also depends on the type and amount of surfactant.

In some embodiments, the shear may be generated as a result of the kinetic energy of the liquid, as the liquid flows through pipes, orifices, channels, etc. The liquid is pressurized (potential energy) and as the liquid flows the potential energy is converted to kinetic energy. In some embodiments, sonication can be used as an energy source. In some embodiments, shear is generated as a result of tiny bubbles moving at high velocities and bursting inside the liquid.

To form the coating over the core particles, the reactants need to react at the surface of the core particles; or the reactants react in the liquid but precipitate on the surface of the core particles. If none of these scenarios apply, the reaction products will form particles in an independent fashion of the core particles.

For the reactants to react at the surface of the particles, one of the reactants may be part of the surface of the core particle. In some embodiments, the surface may catalyze the reaction. If the reaction occurs in the liquid phase, the products would have to coat the surface very quickly after they form, before the products grow into large independent particles. It is therefore essential that the reactants mix at a scale smaller than the core particles, so that the reactants react to form small structures, which eventually form the coating. The timing of the mixing of the reactants in relation to the reaction rate is also important.

When dealing with small particles suspended in liquids, deagglomeration requires a certain amount of energy. A first approximation is given by turbulence theory which is used to estimate this from mixing power input and solution density and viscosity. See, for example, Kolmogorov AN. The Local Structure of Turbulence in Incompressible Viscous Fluid for Very Large Reynolds Numbers. Proc. USSR Acad. Sci. 1941; 30, 299-303.

$$\lambda = \left[\frac{v^3}{\varepsilon}\right]^{1/4}$$

Where v is the kinematic viscosity and ε is the rate of energy dissipation per unit mass in turbulent mixing. This Kolmogorov length, λ, is the length scale that is associated with the size of the smallest eddies formed prior to the dissipation of heat, and associated with the size of the entities being formed; and it also has a significant impact on the time scale for the transport processes involved. This formula shows that the smaller the particles, the larger the energy requirement is.

A common method to deagglomerate the particles suspended in liquid is using High Pressure Homogenization (HPH) or microfluidization methods. Equipment used for these methods is commercially available from companies such as Niro Soavi, Parma, Italy and Microfluidics, Westwood, MA, USA. Examples of pertinent equipment from these companies include PantaPLUS 1000 and 110EH, respectively. One of these pieces of equipment can be utilized to de-agglomerate the particles.

Such equipment involves the pressurization of liquid reactant streams to pressures approaching or exceeding 2000 bars [6-8]. The pressure energy is used to pump the streams through microchannels at velocities over 400 m/s. These high velocities, are responsible for highly turbulent flows, (corresponding to Reynolds numbers of 75,000) with mixing scales of 25-50 nm. The residence times in the high energy zone of the instrument vary in the range of 10-90 microseconds indicating that phenomena down to 25-50 nm have 10-90 microseconds to complete.

Once the particles are de-agglomerated, the liquid stream may be combined with another liquid stream that contains precursors of the coating. However, as mentioned earlier, the mixing method of these streams is important in order to form the actual coating. The mixing with the reactant stream can be done using a mixing device with multiple ports, such as a T-mixer, a microfluidics chip, or a two port homogenization device, such as model CR5 or MMR technology from Microfluidics, Westwood, MA.

The last two devices provide high shear, and in addition the ability to pump two or more fluid stream simultaneously at predetermined rates. Therefore, using the CR5, the particle deagglomeration and the mixing of the reactants may happen in one step.

One way to implement the process of the present disclosure is to use a modified High Pressure Homogenizer (HPH) or a Microfluidizer-type processor [6]. Such devices are commonly used to deagglomerate particles suspended in liquid, or to break up large solid or liquid particles, forming formulations with micron- and nano-sized particles. Equipment used for these methods is commercially available from companies such as Niro Soavi, Parma, Italy, Microfluidics, Westwood, MA, USA and DyHydromatics, Maynard, MA, USA. Examples of pertinent equipment from these companies include PantaPLUS 1000, 110EH and PSI 20 respectively. One of these pieces of equipment can be utilized to de-agglomerate the particles.

For certain embodiments of the present disclosure, it is useful to use the device mentioned above that was modified to also allow for multiple streams of liquids to enter the device. The modification may be done (for example) according to reference [7], or model CR5 or MMR technology from Microfluidics, Westwood, MA, or other homogenizer manufacturer.

The processes described above and the end result are different from the Layer-by-Layer (LbL) fabrication technique described in J. J. Kirkland (1965). "Porous Thin-Layer Modified Glass Bead Supports for Gas Liquid Chromatography". Analytical Chemistry. 37: 1458. doi:10.1021/ac60231a004 and also R. K. Iler (1966). "Multilayers of colloidal particles". Journal of Colloid and Interface Science. 21: 569. doi:10.1016/0095-8522(66)90018-3. That technique consists of depositing alternating layers of oppositely charged materials with wash steps in between. Therefore, it applies only to compounds that carry charges. Following are some key differences between the LbL technique and the processes of the present disclosure:

(a) The LbL method is based on oppositely charged species. In the LbL method, the charges of the particles attract species with opposite charges, which eventually form a layer. The processes of the present disclosure do not depend on the charges of the species to form a layer, so it can be used for species that are not charged. In the processes described herein, the particles to be coated are brought in close proximity with the layering material, as it is being synthesized. Thermodynamics generally favors the adsorption of the layering material onto the particle because the total surface area of the particle and the layering material, along with the surface energy decreases when the layering material forms a layer around the particle, rather than a separate particle. This controls both the location and timing of the layer formation.

When the layers are held together with electrostatic charges only, as is the case of the LbL method, the particle may fall apart when it is used in an environment that has different pH or ionic strength that the environment it was produced. This may be undesirable, because the particle may fall apart prematurely, before it reaches its intended target. In contrast, when layers are not kept together with electric charges only, they are more stable in pH and ionic strength variations. The processes of the present disclosure do not rely on charged species to form a layer. Therefore, they can be used for materials with or without charge.

(b) The LbL method does not specify deagglomeration of the core particles. Deagglomeration is advantageous because it exposes the particle surfaces, so the layers form around the particles.

The following non-limiting examples illustrate certain advantages and improvements of the processes and layered particles of the present disclosure. These examples are meant to be illustrative only and are not intended to limit or preclude other embodiments of the present disclosure.

Example 1: Calcium Phosphate Particles

Stream 1. 5 mg/ml sodium phosphate, 50 ml.
Stream 2. 5 mg/ml calcium chloride, 40 ml.
Stream 1 is poured into the reservoir of a HPH, Model PSI-20 from DyHydromatics, Maynard, MA Stream 2 is siphoned with a pipette. The tip of the pipette is positioned at the outlet of the reservoir. The pressure is set at 20,000 psi. The machine starts and after two to three seconds the pipette handle is depressed such that it dispenses a small amount of Stream 2 during the compression stroke of the machine. After dispensing 20 ml of Stream 2 in 1 min, a sample of 1 ml is taken and the particle size is measured. The particle size analyzer used is a Litesizer 500 dynamic light scattering instrument from Anton Paar, Graz, Austria As more from Stream 2 is dispensed, around 25 ml total, the liquid in the reservoir becomes cloudy. Another sample is obtained for particle size measurements. Dispensing Stream 2 is then stopped while the machine is still working. The liquid does not change in appearance after processing for 10-15 minutes longer.

The particles are highly agglomerated and the agglomerates measure in the micron size range as shown below:

2.288 microns (2288 nm)-after addition of 20 ml of Stream 2
4.666 microns (4666 nm)-after addition of all 40 ml of Stream 2
The primary particle size is less than 200 nm.

Example 2. Calcium Phosphate/RNA Particles

Stream 1. 5 mg/ml sodium phosphate 2.5 mg/ml RNA solution, 50 ml
Stream 2. 5 mg/ml calcium chloride solution, 40 ml
The same equipment as was used in Example 1 is also used in Example 2.

Stream 1 is poured into the machine reservoir. Stream 2 is siphoned with a pipette. The tip of the pipette is positioned at the outlet of the reservoir. The pressure is set at 20,000 psi. The machine starts and after two to three seconds the pipette handle is depressed such that it dispenses a small amount of Stream 2 during the compression stroke of the machine. After dispensing 20 ml of Stream 2 in about 1 minute, a sample (1 ml) is taken and the particle size is measured. As more from Stream 2 is dispensed, the liquid in the reservoir becomes cloudy. Another 1 ml sample is obtained for particle size measurements. Dispensing Stream 2 is then stopped, while the machine is still working. After 2-3 minutes, the sample becomes clear.

The primary particle size is measured readily since the particles are stable (and not agglomerated) for over 1 hr after production, as seen below:

134 nm-after addition of 20 ml of Stream 2
207 nm-after addition of all 40 ml of Stream 2

Example 3. Calcium Phosphate/RNA Particles

This example is similar to Example 2, but with twice the concentrations of the sodium phosphate, RNA and calcium chloride.

Stream 1. 10 mg/ml sodium phosphate 5 mg/ml RNA solution, 50 ml Stream 2. 10 mg/ml calcium chloride solution, 40 ml The same equipment as that used in Example 1 used here.

Stream 1 is poured into the machine reservoir. Stream 2 is siphoned with a pipette. The tip of the pipette is positioned at the outlet of the reservoir. The pressure is set at 20,000 psi. The machine starts and after a few seconds the pipette handle is depressed, so it dispenses a small amount of Stream 2 during the compression stroke of the machine. After dispensing 20 ml of Stream 2 in 1 minute, a sample is taken and the particle size is measured. As more from Stream 2 is dispensed at the same rate as before, the liquid in the reservoir becomes cloudy. Another 1 ml sample is obtained for particle size measurements. Dispensing Stream 2 is then stopped, while the machine is still working. After 2-3 minutes, the sample became clearer.

The primary particle size is measured readily since the particles are stable (and not agglomerated) for over 1 hr after production, as seen below:

184 nm-after addition of 20 ml of Stream 2
1100 nm-after addition of all 40 ml of Stream 2
The primary particle size is less than 200 nm.

Example 4. Calcium Phosphate/RNA Particles

This example is similar to Example 2, but with larger volume of Stream 2.

Stream 1. 10 mg/ml sodium phosphate 5 mg/ml RNA solution, 50 ml

Stream 2. 10 mg/ml calcium chloride solution, 60 ml

The same equipment as that used in Example 1 used in this example.

Stream 1 is poured into the machine reservoir. Stream 2 is siphoned with a pipette. The tip of the pipette is positioned at the outlet of the reservoir. The pressure is set at 20,000 psi. The machine starts and after a few seconds the pipette handle is depressed, so it dispenses a small amount of Stream 2 during the compression stroke of the machine. After dispensing 20 ml of Stream 2 within 45 seconds, an 1 ml sample is taken and the particle size is measured. As more from Stream 2 is dispensed at the same rate as before, the liquid in the reservoir becomes cloudy. Another sample 1 ml sample is obtained for particle size measurements. Dispensing Stream 2 is then stopped, while the machine is still working. After 2-3 minutes, the sample becomes clearer.

The primary particle size is measured readily since the particles are stable (and not agglomerated) for over 1 hr after production, as seen below:

134 nm-after addition of 30 ml of Stream 2
380 nm-after addition of all 40 ml of Stream 2
The primary particle size is 70-150 nm.

After production, the suspension is passed through a 0.22 micron filter to determine if the particles need to be filtered or sterilized, which is essential for injecting the formulation in the body of a human or non-human animal.

REFERENCES

1. M. Ferrari. Nat Rev Cancer, 5(3):161-71 (2005)
2. U.S. Pat. No. 5,533,875
3. Fire A, Xu SQ, Montgomery M K, et. al "Potent and specific genetic interference by double-stranded RNA in *Caenorhabditis elegans*". Nature 1998; 391:806e811.
4. Elizabeth Verena Giger, "Stabilization of Calcium Phosphate Nanoparticles for Transfection of Nucleic Acid Drugs", Dissertation. ETH NO. 20625, Zurich, Switzerland (2012)
5. Yang Yang, Jun Li, Feng Liu and Leaf Huang, "Systemic Delivery of siRNA via LCP Nanoparticle Efficiently Inhibits Lung Metastasis", *The American Society of Gene & Cell Therapy*, www.moleculartherapy.org vol. 20 no. 3, March 2012
6. Microfluidics International, www.microfluidicscorp.com
7. Thomai Panagiotou, Steven V. Mesite and Robert J. Fisher, "Production of Norfloxacin Nanosuspensions Using Microfluidics Reaction Technology (MRT) through Solvent/Antisolvent Crystallization". *Industrial and Engineering Chemistry Research, American Chemical Society*, 48, pp. 1761-1771, 2009
8. Thomai Panagiotou, Kenneth Chomistek and Robert J. Fisher, "Microfluidics Reaction Technology (MRT) for Continuous Production for Nanoformulations of Drug Entities and Advanced Materials", NanoFormulation, pp. 135-149, Edited by Gordon Libby and Reginald Tan, Royal Society of Chemistry Publishing, London 2012
9. Thomai Panagiotou and Robert J. Fisher (2011). Bottom up Nano-particle Formation via Controlled Crystallization and Chemical Reactions. MRS Proceedings, 1353, mrss11-1353-hh04-03 doi:10.1557/opl.2011.1343
10. U.S. Pat. No. 8,187,554
11. T. Panagiotou, S. V. Mesite, J. M. Bernard, K. J. Chomistek, and R. J. Fisher, "Production of Polymer Nanosuspensions, Using Microfluidizer® Processor Based Technologies." NSTI-Nanotech 2008, www.nsti.org, ISBN 978-1-4200-8503-7 Vol. 1, pp. 688-691, 2008.

Each of the abovementioned references are incorporated herein by reference in their entireties.

While embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A process for the preparation of layered particles comprising:
    (a) forming a first liquid stream comprising:
        (i) obtaining a first mixture of immiscible fluids that contains one or more core particles inside a first liquid carrier, wherein the first mixture is an emulsion;
        (ii) optionally, homogenizing the first mixture; and
        (iii) introducing one or more reactants into the first mixture;
    (b) forming a second liquid stream comprising:
        (i) introducing one or more reactants into a second liquid carrier;
        (ii) mixing the one or more reactants in the second liquid carrier to form a second mixture; and
        (iii) optionally, homogenizing the second mixture;
    (c) continuously pumping the first liquid stream into a first port of a multi-port mixing device, wherein the first liquid stream is pumped into the mixing device at a fraction of the flow rate of the mixing device;

(d) continuously pumping the second liquid stream into a second port of the multi-port mixing device; and (e) mixing the first liquid stream and the second liquid stream inside the mixing device for an effective period of time to form a layer on the one or more core particles, wherein the mixing is performed by the mixing device at an energy rate per kilogram of the mixture of liquid streams of from about $10^5$ to about $10^{10}$ W/kg.

2. The process of claim 1, wherein
the process further comprises deagglomerating the core particles.

3. The process of claim 1, wherein:
the effective period of time is from about 1 microsecond to about 1 hour; or
the effective period of time is from about 1 microsecond to about 20 seconds; or
the effective period of time is from about 1 microsecond to about 1 minute.

4. The process of claim 1, wherein
the process further comprises repeating steps (a)(iv) and (b)(iii) to step (e) to increase the thickness of the layer; or
the process further comprises repeating steps (a) to (e) to form a second layer; or
the process further comprises suspending the one or more layered particles in a solution; or
the process further comprises deagglomerating the one or more layered particles; or
the process further comprises filtering the mixture to remove particles having sizes from about 200 nm to about 25 microns; or
the process further comprises sterilizing the mixture; or
the process further comprises lyophilizing the one or more layered particles; or
the process further comprises drying the one or more layered particles; or
the process further comprises heat treating the one or more layered particles.

5. The process of claim 1, wherein:
the one or more reactants in the first liquid stream are acids; or
the one or more reactants in the first liquid stream are bases; or
the one or more reactants in the second liquid stream are bases; or
the one or more reactants in the second liquid stream are acids; or
the one or more reactants in the first liquid stream are acids and the one or more reactants in the second liquid stream are bases and the acids and the bases react to form a salt; or
the one or more reactants in the first liquid stream are bases and the one or more reactants in the second liquid stream are acids and the acids and the bases react to form a salt.

6. The process of claim 1, wherein:
the same liquid is used in the first liquid stream and the second liquid stream; or
a different liquid is used in the first liquid stream and the second liquid stream.

7. The process of claim 1, wherein:
the layered particles comprise particles selected from small molecules, nucleic acids, proteins, peptides, and monoclonal antibodies, and combinations thereof.

8. The process of claim 1, wherein:
one or more active ingredients are encapsulated in the layered particles.

9. The process of claim 1, wherein:
the one or more reactants in the first liquid stream react with the one or more reactants in the second liquid stream when the first liquid stream and second liquid stream are mixed in step (e); or
the one or more reactants in the first liquid stream and the one or more reactants in the second liquid stream contain dissolved salts that precipitate when the salts in the first liquid stream and the salts in the second liquid stream come into contact during mixing step (e).

10. The process of claim 9, wherein:
the salts in the first liquid stream comprise calcium chloride or any other calcium salt and the salts in the second liquid stream comprise sodium phosphate or any other phosphate salt; or
the salts in the first liquid stream comprise sodium phosphate and the salts in the second liquid stream comprise calcium chloride; or
the salts in the first liquid stream comprise calcium chloride and the salts in the second liquid stream comprise sodium carbonate.

11. The process of claim 10, wherein:
the first liquid stream, the second liquid stream, or both the first liquid stream and the second liquid stream further comprise nucleic acids; or
the first liquid stream, the second liquid stream, or both the first liquid stream and the second liquid stream further comprise one or more active pharmaceutical ingredients.

12. The process of claim 1, wherein the liquid carrier in the first liquid stream is aqueous and the liquid carrier in the second liquid stream comprises one or more water miscible organic solvents having one or more polymers or one or more lipids dissolved in the solvents.

13. The process of claim 12, wherein:
the one or more solvents comprise water miscible alcohols or water miscible ketones; or
the one or more solvents are selected from ethanol, methanol, acetone, dimethyl sulfoxide (DMSO), N-Methyl-2-pyrrolidone (NMP), tetrahydrofuran, acetonitrile, and poly(ethylene glycol); or
the one or more polymers are selected from poly(lactic acid) (PLA), poly(lactide-co-glycolide) (PLGA), poly(epsilon-caprolactone) (PCL), starches, polysaccharides, biocompatible polymers, poly(acrylates), and poly(styrene), and derivatives thereof; or
the one or more lipids are selected from cholesterol, phospholipids, cationic lipids, neutral lipids, and sterols, and derivatives thereof; or
the one or more liquids are selected from lipids containing poly(ethylene glycol) (pegylated), fluorescent lipids, and crosslinking lipids; or
the first liquid stream, the second liquid stream, or both the first liquid stream and the second liquid stream further comprise one or more active pharmaceutical ingredients.

14. A process for the preparation of core particles comprising:
(a) forming a first liquid stream comprising:
(i) introducing one or more reactants into a first liquid carrier to form a first liquid stream; and
(ii) optionally, homogenizing the first liquid stream;

(b) forming a second liquid stream comprising:
  (i) introducing one or more reactants into a second liquid carrier to form a second liquid stream; and
  (ii) optionally, homogenizing the second liquid stream;
(c) pumping the first liquid stream into a first port of a multi-port mixing device;
(d) pumping the second liquid stream into a second port of the multi-port mixing device;
(e) mixing the first liquid stream and the second liquid stream to form one or more core particles, wherein the mixing device is capable of producing an average energy rate per kilogram of the mixture of liquid streams of from about $10^5$ to about $10^{10}$ w/kg; and
(f) utilizing the core particles to prepare layered particles comprising the steps of:
  (i) forming a first liquid stream comprising:
    (1) obtaining a first mixture of immiscible fluids that contains one or more core particles inside a first liquid carrier, wherein the first mixture is an emulsion;
    (2) optionally, homogenizing the first mixture; and
    (3) introducing one or more reactants into the first mixture;
  (ii) forming a second liquid stream comprising:
    (1) introducing one or more reactants into a second liquid carrier;
    (2) mixing the one or more reactants in the second liquid carrier to form a second mixture; and
    (3) optionally, homogenizing the second mixture;
  (iii) continuously pumping the first liquid stream into a first port of a multi-port mixing device, wherein the first liquid stream is pumped into the mixing device at a fraction of the flow rate of the mixing device;
  (iv) continuously pumping the second liquid stream into a second port of the multi-port mixing device; and
  (v) mixing the first liquid stream and the second liquid stream inside the mixing device for an effective period of time to form a layer on the one or more core particles, wherein the mixing is performed by the mixing device at an energy rate per kilogram of the mixture of liquid streams of from about $10^5$ to about $10^{10}$ W/kg.

15. The process of claim 1, wherein:
the fraction of the flow rate of the mixing device is from about 0.0001 to about 0.9; or
the fraction is from about 0.001 to about 0.9.

16. The process of claim 1, wherein:
the one or more core particles are present in the mixture of liquid streams of step (e) in an amount of from about 0.01% to about 50% (weight of the one or more core particles/(weight of the one or more core particles plus the liquid stream mixture of step (e))); or
the one or more core particles are present in the mixture of liquid streams of step (e) in an amount of from about 2% to about 50% (weight of the one or more core particles/(weight of the one or more core particles plus the liquid stream mixture of step (e))); or
the one or more core particles are present in the mixture of liquid streams of step (e) in an amount of from about 5% to about 50% (weight of the one or more core particles/(weight of the one or more core particles plus the liquid stream mixture of step (e))); or
the one or more core particles are present in the mixture of liquid streams of step (e) in an amount of from about 2% to about 40% (weight of the one or more core particles/(weight of the one or more core particles plus the liquid stream mixture of step (e))).

17. The process of claim 1, wherein:
the homogenizing of steps 1(a)(iii) and 1(b)(iii) is performed at a pressure of from about 500 psi to about 45,000 psi; or
the homogenizing of steps 1(a)(iii) and 1(b)(iii) is performed at a pressure of from about 3,000 psi to about 30,000 psi.

18. The process of claim 1, wherein the mixing device further comprises a homogenizer or a rotor-stator mixer that has a processing module, and wherein:
the residence time in the processing module of the mixing device is from about 1 microsecond to about 1 millisecond; or
the residence time in the processing module of the mixing device is from about 2 microseconds to about 100 microseconds, or
the residence time in the processing module of the mixing device is from about 10 microseconds to about 90 microseconds; or
the residence time in the processing module of the mixing device is from about 10 microseconds to about 25 microseconds.

19. The process of claim 1, wherein the one or more core particles introduced into the first liquid carrier in (a)(i) are the same as the one or more reactants introduced into the first mixture in (a)(iv).

* * * * *